United States Patent [19]

Weinblatt

[11] Patent Number: 4,528,989
[45] Date of Patent: Jul. 16, 1985

[54] SCREENING METHOD FOR MONITORING PHYSIOLOGICAL VARIABLES

[76] Inventor: Lee S. Weinblatt, 797 Winthrop Ave., Teaneck, N.J. 07666

[21] Appl. No.: 437,811

[22] Filed: Oct. 29, 1982

[51] Int. Cl.$^3$ .............................................. A61B 5/00
[52] U.S. Cl. ..................................... 128/745; 351/210
[58] Field of Search ....................... 128/745, 731–732, 128/782; 351/209–210, 245

[56] References Cited

U.S. PATENT DOCUMENTS

| | | | |
|---|---|---|---|
| 3,158,431 | 11/1964 | Gutjahr et al. ................. | 128/745 X |
| 3,288,546 | 11/1966 | Gans ................................ | 128/745 X |
| 3,416,857 | 12/1968 | Lookabaugh .................... | 128/745 X |
| 3,542,457 | 11/1970 | Balding et al. ................. | 351/209 X |
| 3,842,822 | 10/1974 | Levinson et al. ................ | 128/745 |
| 4,075,657 | 2/1978 | Weinblatt ........................ | 351/210 X |
| 4,094,307 | 6/1978 | Young, Jr. ....................... | 128/731 |
| 4,331,132 | 5/1982 | Mukasa ........................... | 128/745 X |

FOREIGN PATENT DOCUMENTS

| | | | |
|---|---|---|---|
| 3011746 | 10/1981 | Fed. Rep. of Germany ...... | 128/745 |
| 514273 | 6/1976 | U.S.S.R. .............................. | 351/210 |

OTHER PUBLICATIONS

Pavlidis; "Do Eye Movements Hold the Key to Dyslexia?"; *Neurophysiology*, vol. 19, pp. 57–64.

Mackworth et al.; "Eye Fixations Recorded on Changing Visual Scenes by the TV Eye-Marker"; *J. of the Optical Soc. of Amer.*, vol. 48, No. 7, 7-1958, pp. 439–445.

Wilsher et al.; "Piracetam as an Aid to Learning in Dyslexia"; *Psycho Pharmacology*, vol. 63, pp. 107–109, (1979).

*Primary Examiner*—Lee S. Cohen
*Assistant Examiner*—Angela D. Sykes
*Attorney, Agent, or Firm*—Natter & Natter

[57] ABSTRACT

A screening method and apparatus suitable for diagnosing dyslexia which includes a television camera for detecting reflected light to track eye movements in response to projected visual stimuli. The loci of said eye movements are superimposed over the visual stimuli on a TV monitor and also recorded. In addition, corresponding brain wave activity can be scanned and correlated with the eye movements.

9 Claims, 2 Drawing Figures

SCREENING METHOD FOR MONITORING PHYSIOLOGICAL VARIABLES

TECHNICAL FIELD

This invention concerns a system for diagnostic testing and especially a screening method and apparatus for detecting physiological dysfunctions.

In particular, the invention relates to an electro-optical system for monitoring eye movement and concomitant neurophysiological activity in response to visual stimuli with particular application to diagnosing dyslexia.

BACKGROUND ART

It has been generally recognized that an underlying cause of many learning disabilities is attributable to abnormal sensory integration and the capacity to receive, retain and correctly interpret visual information. Unfortunately, the determination of the exact nature of this disfunction has in many aspects been inconclusive and the diagnosis thereof somewhat difficult to discern. A dyslexic child, for example, typically exhibits an inability to comprehend one or more of the following: sound/symbol relationships, spelling, word patterns, sequences and combinations of letters. Although the problem had been considered as associated with emotional disturbances, biochemical imbalances, maturational lag, and brian lesions, recent studies pointed to a central malfunction in dyslexics, namely sequential disability and/or oculomotor malfunction. The results of such study were published by Dr. George Th. Pavlidis in a paper entitled *Do Eye Movements Hold the Key to Dyslexia?*, Dept. of Psychology, University of Manchester, Manchester, England (May 23, 1980). Testing methods were developed for measuring erratic eye movement patterns which were found to be characteristic of dyslexics during reading and nonreading sequential tasks. These prior tests, however, were primarily directed to the measurement and recording of very small or micro movements of the subject's eye and involved the use of photoelectric cell devices which were positioned in close proximity to the eye. A disadvantage of those early attempts for monitoring eye movement was that the minute or ultrafine ocular displacements did not provide sufficient information for analyzing the scanning eye movement which was of greater magnitude and occurred under actual reading conditions. Another shortcoming of those testing methods was that the resultant eye movement pattern was not juxtaposed over the visual stimuli so that eye movement could be tracked and recorded for determining the extent of the deviations in eye scanning patterns or other ocular motor malfunctions in response to specific stimuli.

Other prior art apparatus concerned with tracking eye movement utilized a separate light source for directing an incident ray at the viewer's eye and also employed a receiving camera for detecting the reflected light ray. A problem with the aforementioned system is that the incident ray presented a distraction—if not an annoyance—to the viewer, and the receiving camera which was positioned adjacent the viewer was similarly disconcerting.

Another drawback of the prior art reflected beam concept was that corneal aberrations were magnified in the reflected ray and thus did not present an accurate representation of the direction and magnitude of eye movement.

It should be further noted that the devices of the prior art were also primarily directed to detecting eye movement, whereas the instant invention provides a more comprehensive scanning approach.

DISCLOSURE OF THE INVENTION

Briefly, the nature of this invention involves a method for tracking and recording eye movement and cerebral activity in response to the presentation of a prerecorded array of indicia on a projection screen.

The apparatus for accomplishing these purposes includes a television receiver and videotape recorder for feeding programmed stimuli to be viewed by the subject. The present invention eliminates the need for a separate light source by incorporating a high sensitivity television camera which effectively receives corneally reflected light emanating from the television screen. As a further improvement, the television camera is positioned out of the line of sight of the viewer and the corneally reflected beam is received in a fiber optics collecting tube for transmission to the television camera. The camera output signals are combined with the signal from the videotape recorder and then fed to a display monitor such as a television set and/or videotape recorder. The eye movements detected by the television camera will appear in the form of a "dot" pattern superimposed upon the visual stimuli of the videotape recorder.

An additional measure incorporated into the device of the present invention for improving calibration and for compensating corneal aberrations includes the application of a zoom lens on the receiving television camera.

A still further aspect of this invention is directed to the simultaneous monitoring of neurological acitivity in each of the cerebral hemispheres of the viewer. This is accomplished by electrodes applied to the viewer's scalp and connected to electroencephalographic amplifying and recording apparatus.

To provide improved accuracy and to minimize false readings due to movement of the viewer's head, a motion detecting microswitch and circuit is incorporated into a head support apparatus for the purpose of signalling head movement vis-a-vis eye movement of the subject.

It should be observed that the method and apparatus of this invention will provide a more comprehensive system for detecting physiological information regarding the correlation between eye movement and cerebral activity as an adjunct to the diagnosis of dyslexia.

In view of the foregoing, it should be apparent that the present invention overcomes many of the shortcomings of the prior art and provides an improved screening system and apparatus for detecting physiological dysfunctions such as dyslexia.

Having thus summarized the invention, it will be seen that it is an object thereof to provide a screening method and apparatus for detecting physiological variables of the general character described herein which is not subject to the aforementioned disadvantages.

Another object of this invention is to provide a method and apparatus having the capability of simultaneously monitoring the physiological variables of eye movement and cerebral activity.

Specifically, it is an object of this invention to provide a screening method for evaluating dyslexia by using electro-optical apparatus for generating a dot pattern indicative of eye movement.

A still further object of this invention is to provide a system for tracking eye movement under actual testing conditions by superimposing the dot pattern upon programmed visual stimuli.

Yet another object of this invention is to provide for the introduction of brain wave data for comparative analysis in conjunction with eye movement.

With these ends in view, the invention finds embodiment in certain combinations of elements and arrangements of parts by which the object aforementioned and certain other objects are hereinafter attained, all as more fully described with reference to the accompanying drawings and the scope of which is more particularly pointed and indicated in the appended claims.

BRIEF DESCRIPTION OF THE DRAWINGS

In the accompanying drawings in which is shown a possible exemplary embodiment of the invention.

BEST MODE FOR CARRYING OUT THE INVENTION

Figure 1:
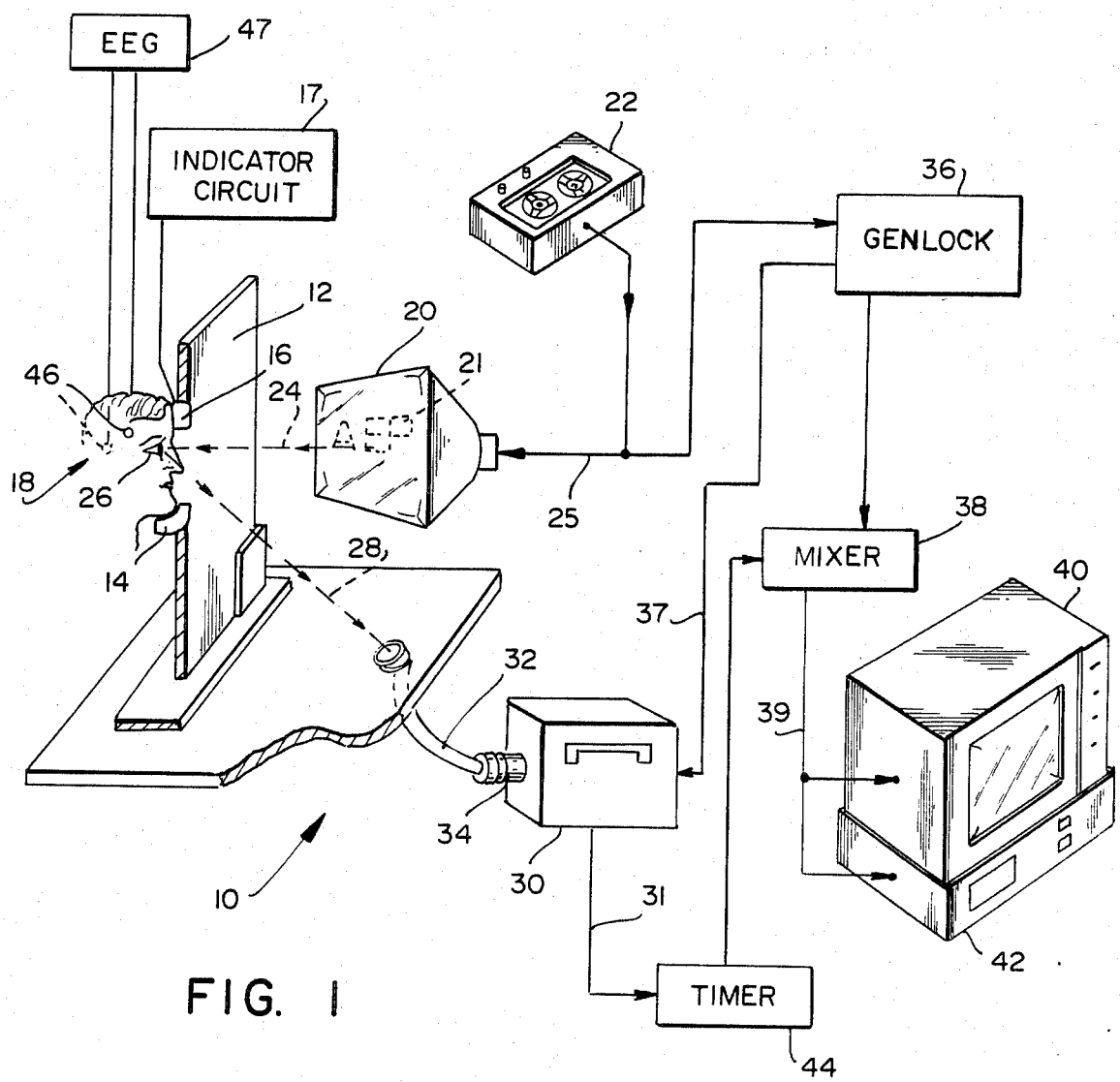
FIG. 1 is a pictorial representation of the method and apparatus of this invention.

Referring now in detail the drawings, the reference numeral 10 denotes generally the apparatus of this invention for detecting physiologic disfunctions in accordance with the method disclosed.

The apparatus 10 as illustrated in FIG. 1 includes a viewing stand 12 having a chin cup 14 and a movement detector 16. The viewing stand 12 is adapted for accurately positioning a head 18 of the individual to be tested. The head movement detector 16 preferably incorporates a conventional microswitch and indicator circuit 17 for denoting movement of the head 18 which would adversely affect the test results and can be indicated by a visual signal.

As further illustrated in FIG. 1, a television receiver 20 (TV) positioned within the subject viewer's line of sight and is spaced at a comfortable distance from the viewer. Selected visual stimuli 21 designed for optical tracking by the viewer are programmed for playback from a videotape recording 22 (VTR) and rebroadcast through the TV 20. Incident light from the televised images as typically indicated by ray 24 is reflected from each eye 26 of the viewer as denoted by the reflected ray 28.

A television camera 30 is positioned at a distance from the viewer and preferably concealed from the viewer's sight. A fiber optics collecting tube 32 is utilized for transmitting the reflected ray 28 to the camera 30. It should be noted that camera 30 includes the optics necessary for focussing the ray and maximizing its brightness. Preferably a high sensitivity TV camera is employed for this purpose. In addition, the camera 30 incorporates an image reversing circuit since the output signal shows the eye position in reverse orientation. It should thus be apparent that camera 30 will register eye position in the form of a pair of dots 23 generated by the reflected ray 28. It should additionally be noted that the television camera 30 is provided with a zoom lens 34 for providing compensating corrections for corneal aberrations as will hereinafter be described.

Returning once again to the VTR 22, an output signal 25 is fed to the input of the TV receiver 20 and simultaneously the same signal is input through a Genlock circuit 36 to a mixer 38 which also receives a video output signal 31. By way of background it should be noted that the VTR output 25 is a composite signal of the recorded video signal and the sync signal internal to the VTR. Similarly, the camera output signal 31 is a composite video signal and the sync signal which controls camera functions. Since the mixer 38 is incapable of combining two such signals, the Genlock circuit 36 is utilized. This circuit 36 provides a system for regenerating synchronizing pulses and a circuit subcarrier from a composite video source. In the instant application, the Genlock circuit 36 separates the sync signals from the rest of the taped signals, and the sync signals are then used as a basis for providing a sync input signal 37 to the television camera 30.

Figure 2:
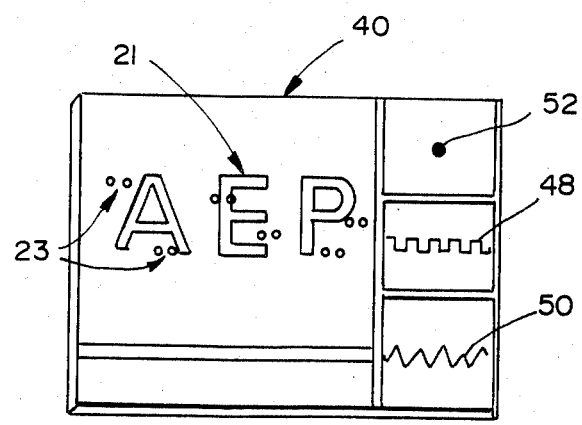
FIG. 2 is a representation of a monitor showing typical test results.

As previously mentioned, an aspect of this invention is the ability to analyze the eye movement pattern superimposed upon the visual stimuli. The mixer 38 can now combine the video signal 31 from the TV camera 30 and the VTR output signal. A timer unit 44 has also been incorporated into the circuitry in series with camera 30 and mixer 38. In this arrangement, the timing signal is combined with the video signal from TV camera 30 and will be synchronized with the videotape recorder 22 so that it begins its timing operation as soon as the visual stimuli are displayed to the viewer. The output signal 39 from the mixer 38 is then fed to a television monitor 40 and a videotape recorder 42. It should be noted that the dot pattern 23 may appear in different locations on the TV monitor 40 as the result of differences in eye curvature. This can be compensated for by having the viewer fix his eyes at a given corner of the screen of the television 20 and by adjustment of the zoom lens 34 to bring the dot pattern 23 where it should be and thereby calibrate the equipment. The dot pattern 23 as noted will be superimposed over the visual stimuli 21 as shown in FIG. 2.

Concerning next the detection of cerebral activity, this is sensed through the use of electrodes 46 applied to the head 18 particularly at the surface of the scalp in accordance with accepted positions. A conventional electrical voltage is transduced from the scalp to differential input amplifiers in order to drive an electroencephalographic recording instrument 47 in a known manner. Further, in accordance with the testing methods of this invention, particular attention is concerned with the difference in activity between the left and right hemispherical lobes and data with regard to same is displayed as typically shown in FIG. 2 at 48, 50. Apparently, the cognitive processes involve neurological activity within the left hemisphere. This information may therefore provide a significant diagnostic tool in conjunction with corresponding eye movement activity. The console monitor 40 also includes a a signal lamp 52 as part of the indicator circuit 17 for detecting head movement of the viewer and for displaying same on monitor 40.

By way of example, typical equipment which can be used is a Sony Model SLO 232VTR and a Sanyo 160X electrically driven black and white TV camera with custom reverse adaptor; the fiber optics is obtainable from Visual Methods Inc.; and the timer is manufactured by Thalmer Electronics Labs, Warrington, Pa. (Model VC 405X). The mixer and Genlock can both be acquired as off-the-shelf components.

The testing method involves the following procedure. The viewer's head is positioned within the viewing stand with the chin positioned in the chin cup and the movement detector affixed to the forehead. The electrodes for the electroencephalograph equipment are affixed to the left and right side of the scalp. Adjustments may be required with regard to the positioning of the viewer's head within the viewing stand, as well as the positioning of the television receiver such that the incident and reflected rays will be in alignment with the fiber optic collecting tube of the TV camera 30. The calibration for compensating for eye aberrations is then performed using zoom lens 34. The videotape recorder 22 and timer 44 are simultaneously activated together with videotape recorder 42. The prerecorded stimuli are then projected on the television screen 20. If it is also desired to monitor electroencephalographic data, that circuitry can also simultaneously activate it.

It should thus be seen that the screening method and apparatus for detecting physiologic dysfunctions of this invention provides an improved and efficient method and device for diagnosing dyslexia and is well adapted to meet the conditions of practical usage.

Since various possible embodiments may be made of the invention and further changes may be incorporated in the exemplary embodiment and method set forth herein, it is to be understood that all material set forth or shown in the accompanying drawings is to be interpreted as illustrative and not in a limiting sense.

Having thus described the invention, there is claimed as new and desired to be secured by Letters Patent:

1. A screening method for monitoring physiological variables of a test subject which is suitable for diagnosing dyslexia including the steps of:
   (a) positioning the head of the test subject utilizing a head movement restraint;
   (b) presenting an array of visual stimuli within the test subject's field of view;
   (c) tracking eye movement of the test subject as targeted upon the stimuli using reflected light rays from the eye of the test subject with said reflected light rays providing a pattern of eye movements;
   (d) superimposing the locus of said eye movements upon the visual stimuli;
   (e) analyzing said eye movement patterns as simultaneously registered on the visual stimuli; and
   (f) evaluating deviations of said eye movement patterns as responsive to discrete stimuli in said array for diagnosing dyslexia.

2. A screening method as claimed in claim 1 further including the step of:
   (g) concomitantly scanning brain wave activity for neurological responses corresponding to the viewed stimuli.

3. A screening method as claimed in claim 2 wherein the brain wave activity is scanned using electroencephalographic apparatus for discerning differences between the brain's left and right hemispherical lobes as a measure of the test subject's cognitive processes.

4. A screening method as claimed in claim 2 wherein the reflected light rays from the test subject's eyes are detected by a concealed television camera.

5. A screening method as claimed in claim 4 wherein the reflected light rays are transmitted by a fiber optics collecting tube to the television camera.

6. A screening method as claimed in claim 4 further including the step of:
   (h) calibrating a variable focal length lens of television camera to compensate for corneal aberrations of the test subject and corresponding deviations in the reflected light rays.

7. A screening method as claimed in claim 4 further including the step of:
   (h) monitoring head movement of the test subject to eliminate erroneous eye movement readings.

8. A screening method as claimed in claim 7 wherein the array of visual stimuli originate from a prerecorded videotape and are presented on a television screen.

9. A screening method as claimed in claim 8 wherein the eye movement are registered with the stimuli to provide a superimposed image by synchronizing and combining output pulses from the videotape and television camera.

* * * * *